United States Patent [19]

Feild

[11] 4,445,517
[45] May 1, 1984

[54] SUCTION DISSECTOR

[76] Inventor: James R. Feild, 2254 N. Parkway, Memphis, Tenn. 38112

[21] Appl. No.: 306,563

[22] Filed: Sep. 28, 1981

[51] Int. Cl.³ .......................................... A61B 10/00
[52] U.S. Cl. .................................... 128/752; 604/35; 604/118
[58] Field of Search ........................ 128/749, 752–753, 128/757–758, 303.13–303.15, 303.17–303.18; 604/27, 30, 35–36, 118–119, 164, 173, 181, 187, 256, 317, 902

[56] References Cited

U.S. PATENT DOCUMENTS

| | | | |
|---|---|---|---|
| 3,469,582 | 9/1969 | Jackson | 604/119 |
| 3,561,429 | 2/1971 | Jewett et al. | 128/752 |
| 3,913,584 | 10/1975 | Walchle et al. | 604/164 X |
| 3,974,833 | 8/1976 | Durden | 604/20 |
| 3,995,619 | 12/1976 | Glatzer | 128/749 X |

FOREIGN PATENT DOCUMENTS 2457862  7/1975  Fed. Rep. of Germany ...... 128/753
2235669  1/1975  France ............................ 128/303.17

OTHER PUBLICATIONS

V. Mueller; "The Surgical Armamentarium"; Neurosurgical Instruments, 1973, pp. 723 and 753.

*Primary Examiner*—Lee S. Cohen
*Assistant Examiner*—Angela D. Sykes
*Attorney, Agent, or Firm*—Donald L. Barbeau

[57] ABSTRACT

An improved surgical device having unique aspiration and instrument control is disclosed. The device is adapted for one-handed simultaneous or alternate dissection and aspiration through a novel combination of control elements. The device is particularly well-suited for neurosurgery and microsurgery.

12 Claims, 10 Drawing Figures

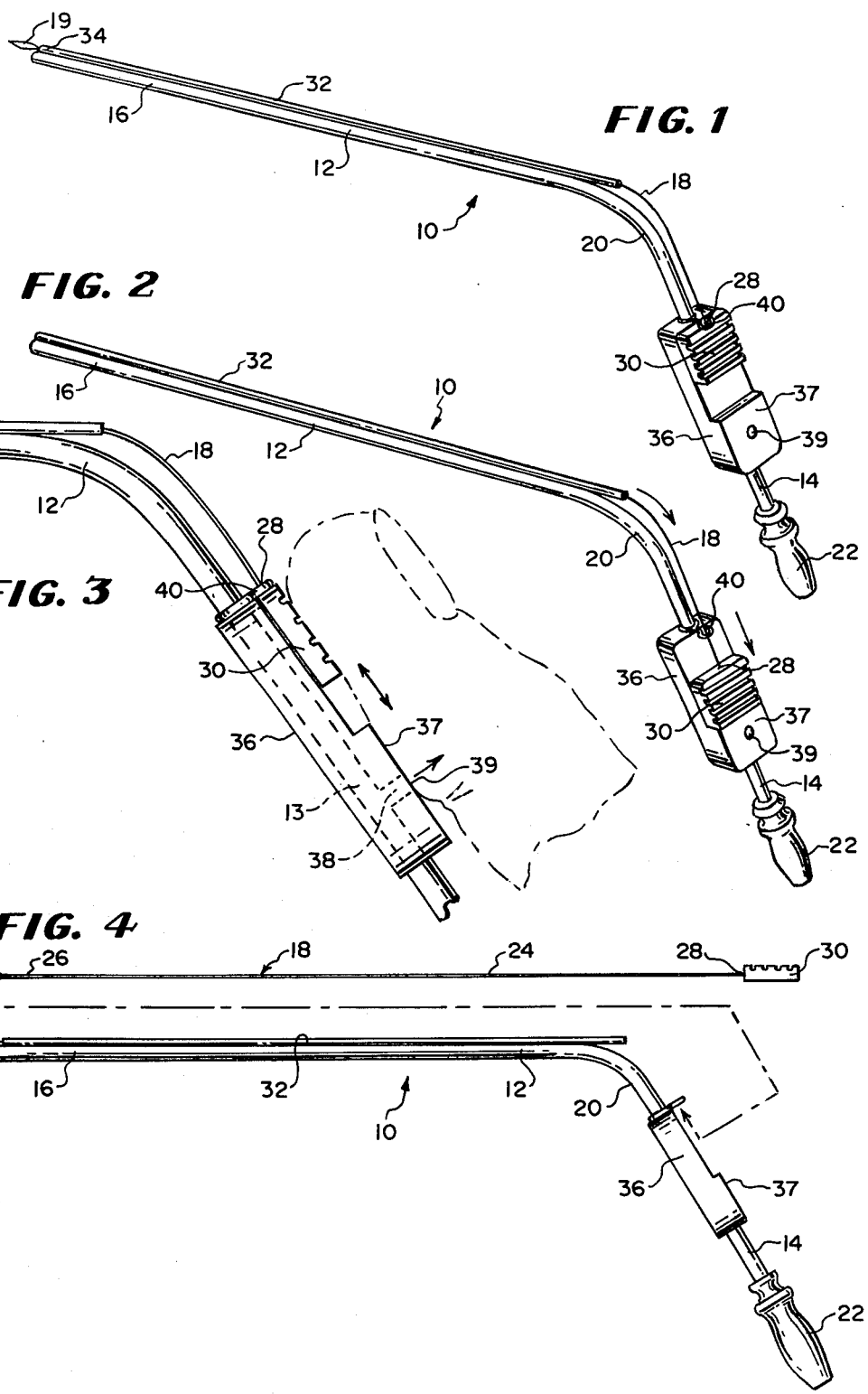

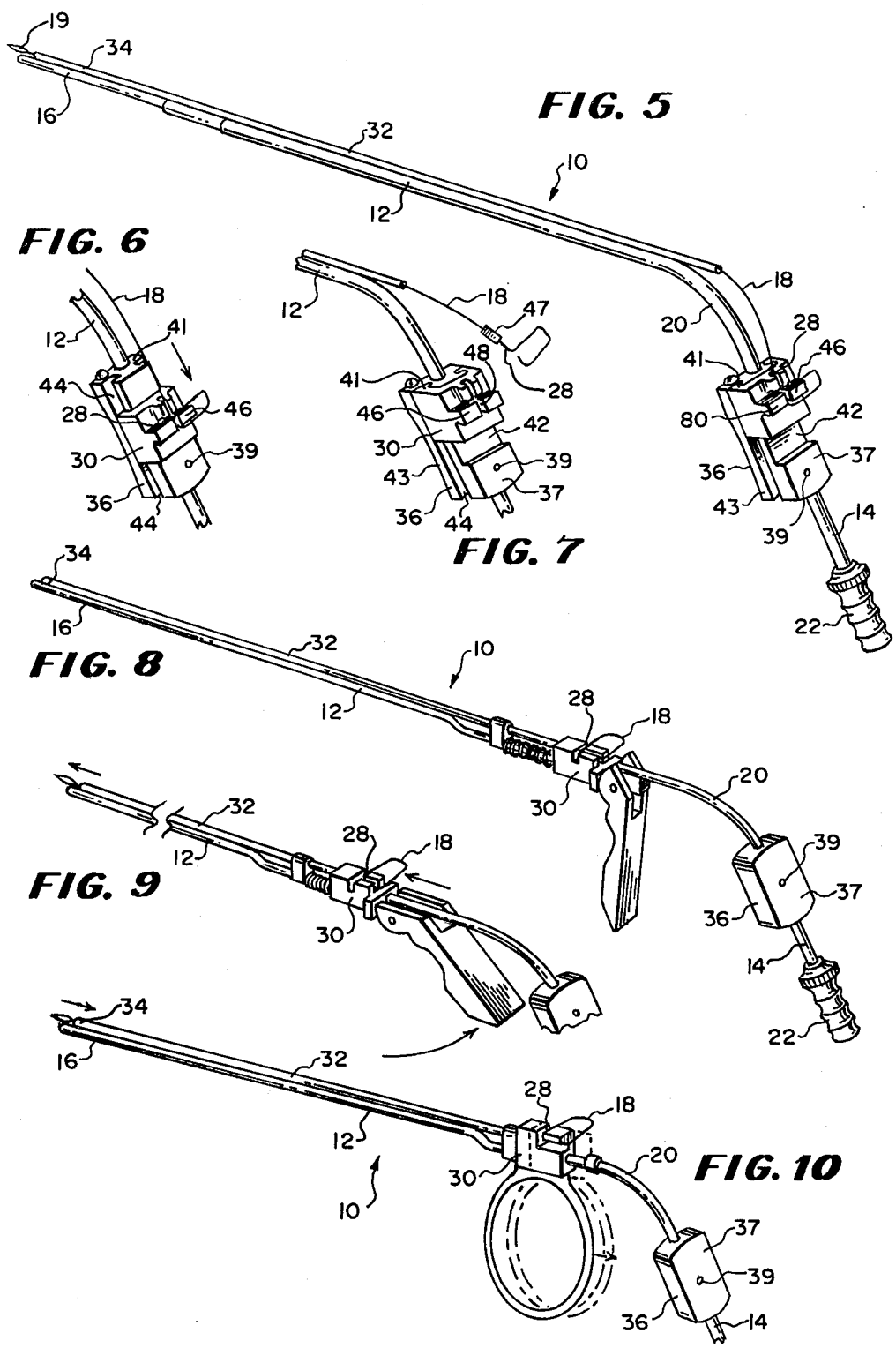

SUCTION DISSECTOR

BACKGROUND OF THE INVENTION

This invention relates to surgical instruments, and in particular to improved multi-functional surgical instruments particularly well-suited for microsurgical procedures. Multi-functional surgical instruments currently available, such as biopsy tools and tissue extractors having suction attachments for aspiration, have provided surgeons with a rapid and facile means for performing routine operations. These instruments have taken on a number of varied configurations, each adapted for the specific requirements of the desired surgical procedure.

Many of the presently available instruments of this type are bulky and cumbersome and are not designed for the new field of microsurgery, and do not provide adequate control of aspiration during the surgical operation. Although such multi-functional instruments are designed to cut and hold biopsy samples and are generally believed to be adequate for obtaining biopsies, they are not acceptable for microsurgery and aneurysm surgery requiring accurate and delicate manipulation of the instrument. Many of the currently available instruments for performing complex surgical procedures cannot adequately control the magnitude of suction within the instrument and thus present a considerable risk of rupturing healthy tissue by drawing too much tissue to the tip of the instrument during aspiration. In addition, many of these instruments have no positive control over operation of the cutting means and thus tissue is only randomly and sometimes accidentally severed.

Heretofore, there has not been an instrument available to the surgeon for providing flexibility of surgical dissections coupled with the simultaneous control of aspiration; or an instrument capable of safe, precise, and accurate manipulation at the operating site.

SUMMARY OF THE INVENTION

In accordance with the present invention, disclosed is a surgical device having an elongated suction housing, and a surgical instrument which is reversibly positioned therewith for bi-directional longitudinal movement along at least a portion of said housing; a means for alternately or simultaneously controlling the bi-directional movement of said instrument and the magnitude of suction within said housing, said means comprising a platform disposed at a proximal end portion of said tube; a first means associated with said platform for adjusting the magnitude of suction within the housing; and a second means associated with said platform and adjacent to said suction adjusting means, for slidably positioning the surgical instrument along said housing.

BRIEF DESCRIPTION OF THE DRAWINGS

FIG. 1 is a perspective view of the surgical device in accordance with one embodiment of the present invention having an extended surgical blade;

FIG. 2 is a perspective view of a device in FIG. 1 having a retracted surgical blade;

FIG. 3 is a fragmentary view of the surgical device in accordance with one embodiment of the present invention showing the cooperative relationship of a surgeon's thumb with the instrument control and vacuum control means;

FIG. 4 is an exploded side view of the device shown in FIGS. 1 and 2;

FIG. 5 is a perspective view of the surgical device in accordance with an alternate embodiment of the present invention;

FIG. 6 is a fragmentary view of the suction and instrument control means associated with the device shown in FIG. 5 having the instrument secured;

FIG. 7 is a fragmentary view of the suction and instrument control means associated with the device shown in FIG. 5 having the instrument detached;

FIG. 8 is a perspective view of an alternate embodiment of the present invention;

FIG. 9 is a fragmentary view of the instrument control means showing the instrument in an extended position in the device shown in FIG. 8;

FIG. 10 is a perspective view of an alternate embodiment of the present invention.

DETAILED DESCRIPTION OF THE PREFERRED EMBODIMENT

Referring to FIGS. 1 through 10, the surgical device in accordance with the present invention is generally shown at 10 and includes an elongated housing 12 defining a suction passageway having a proximal 14 and distal end portion 16; and a reversibly positioned surgical instrument 18 associated therewith. In the preferred embodiment of the present invention, the elongated housing 12 has an arcuate portion 20 disposed near the proximal end portion 14 in order to provide a hand-held instrument which is easily grasped by the surgeon.

In accordance with a preferred embodiment of the present invention, the elongated housing 12 is open at both ends in order to allow debris or fluids to easily pass therethrough. Disposed at the proximal end portion 14 of the housing is a means for applying suction to the passageway 13 defined therein. In one embodiment of the present invention, a standard hose connector 22 is employed. The housing 12 is constructed of plastic or metal in any shape and size depending upon the ultimate intended use of the device, whether it be for macro or microsurgery. The housing is preferably rectangular of cylindrical, and most preferably cylindrical.

The surgical instrument 18 associated with the device of the present invention is shown in FIGS. 1 through 10 and more fully in FIG. 4 having an elongated shaft 24, preferably of metal wire, generally having a length slightly less than the length of the housing. Disposed at the distal end 26 of the shaft 24 is a functional part 19 of the instrument 18. Configurations of the functional part 19 of the instrument in accordance with the present invention include knife blades, spatulas, hooks, blunt dissector chisels, retractors, probes, scoops, trocars, scrapers, snares, gas/liquid delivery ports, and the like. In accordance with the present invention, the preferred configuration is a knife blade as shown in FIGS. 1, 4, 5, 9, and 10.

In a preferred embodiment, the distal portion of the instrument will be the most advanced portion from the surgeon and is preferably very small and very sharp. Disposed at the proximal end 28 of the instrument shaft 24 is a means for actuating its movement along the housing. In the preferred embodiment of the present invention, this means is an instrument actuating member 30 secured to the end of the shaft 24. The various types of actuating members 30 will be discussed in detail below.

The instrument 18 of the present invention is positioned either within the elongated housing 12, in a trough or recess at the surface of the housing 12, or outside of the housing 12 as shown in FIGS. 1 through 10. If the instrument 18 is positioned outside of the housing as shown in the drawings, a means for enclosing the instrument is provided to shield the dissector and prevent the instrument from accidentally cutting healthy tissue during entry to the operating site. In the preferred embodiment of the present invention, the enclosing means comprises an elongated sheath 32 mounted on said housing, said sheath extending substantially the length of the distal portion of said housing. In one embodiment of the present invention, the termination of the distal end 34 of the sheath 32 is positioned immediately rearward of the termination of the distal end portion 16 of the housing 12 so as not to obstruct the surgeon's vision and to allow better viewing of the instrument during surgery.

The surgical instrument of the present invention is reversibly positioned on the elongated housing 12 for bi-directional longitudinal movement along at least a portion of said housing 12 as shown in FIGS. 1 through 3. This allows the blade to be retracted to a position either within the housing 12 or protective sheath 32 to prevent accidental cutting or tissue damage when the blade is not employed in the surgical procedure.

An important feature of the present invention, and one which represents a distinct advantage over the multi-functional surgical instruments currently available, is the ability of the device to provide alternate or simultaneous dissection and aspiration. The unique combination of instrument control and suction control in the present invention adds flexibility to the surgeon and surgical dissections which is not presently available with other surgical devices. Illustrative of this is in a common neurosurgical procedure where the neurosurgeon, having a retractor in one hand and the surgical device of the present invention in the other hand, approaches the area of the brain that houses the pathology. The hand holding the retractor can move the brain out of the way of the surgical device, while the device removes the spinal fluid and the knife blade simultaneously dissects the adhesions of the arachnoid between the brain and the surrounding membrane. In rupturing aneurysms for example, the present device can be held in one hand while an aneurysm clip can be held in the other so that the aneurysm can be ruptured and aspirated almost simultaneously while the clip is applied with the other hand. Although the present device has a definite advantage in microsurgery and aneurysm surgery, it can also be used in all forms of surgery due to its unique combined suction and instrument control which can easily be operated in one hand leaving the surgeon's other hand available for retraction as he advances to the area of interest.

The unique combination and relative positioning of the instrument control and suction control means in accordance with the preferred embodiment of the present invention includes a means disposed at the proximal end of the housing 12 for controlling the magnitude of suction within the passageway 13; a means associated with the suction control means for controlling the bi-directional, longitudinal movement of a surgical instrument 18 along said housing 12; and a means associated with said instrument control means for controlling the disposition of the instrument along its longitudinal path.

In accordance with the present invention, the instrument control, suction control, and disposition control are positioned in close proximity for cooperative operation, and preferably in a raised platform 36. Preferably the platform is rectangular and disposed within the proximal end portion of said housing 12 between the arcuate portion 20 and the proximal end as shown in FIGS. 1 through 7.

The means for controlling suction within the passageway defined by housing 12 is preferably positioned on the upper surface 37 of platform 36. The suction controlling means in accordance with the preferred embodiment of the present invention comprises a second passageway 38 extending orthogonally from the surface of the platform 36 to the passageway 13 in the elongated housing 12. A button member can be used to occlude passageway 13 when it is depressed, or the second passageway can be left open such that the reversible occlusion of the opening 39 of the passageway 38 with a thumb or finger proportionately adjusts the magnitude of suction within the passageway.

The positioning of the instrument 18 along the housing 12 is accomplished by simple manipulation by a surgeon's finger as shown in FIGS. 8 through 10, or thumb as shown in FIGS. 1 through 7. Movement of the instrument 18 by a thumb or finger is accomplished through contact of the actuating member 30 as previously described. Although several types of means for controlling the movement of the instrument can be used, thumb actuation is preferred in accordance with the present invention since it gives more positive control over the handling of the device during microsurgery.

In handling the device in accordance with the preferred embodiment of the present invention, the thumb is placed on the platform 36 over the opening 39 to control the magnitude of the suction as shown by phantom lines in FIG. 3. The thumb is either parallel at an acute angle, or at a right angle to the platform. During the procedure, the thumb is over the hole 39 to occlude the passageway 38 and is removed to decrease the amount of aspiration. The proximal control of the instrument 18 movement should be in or around the platform 36 such that the surgeon is able to control the movement of the instrument without much change in the position of the thumb on the platform 36. In microsurgery, finger motion produces most of the desired movement of the hand, whereas in other types of surgery, the forearm or wrist motion does the work. Therefore, the proximal control of the instrument 18 should be around the platform 36 where the thumb can reach it by moving a small distance. This distance preferably being only a few millimeters.

In a preferred embodiment of the present invention, the positioning of the instrument 18 is controlled at the platform 36 as described above. Preferably the positioning means associated with the instrument 18 includes a recess in the forward upper surface of the platform 36 having a configuration substantially complementary to the actuating means 30 disposed at the proximal end 28 of the instrument. Most preferably, the actuating means 30 and recess are rectangular. Associated with the actuating means 30 is a means for controlling the disposition of the instrument along its longitudinal path. Preferably, this is a guide member 40 disposed at the forward end of the recess. The guide member 40 has a passageway allowing longitudinal movement of the instrument 18 therethrough while at the same time has a retaining member for preventing the outward deviation of the instrument actuating means 30 from the platform 36. In the preferred embodiment, the guide member 40 is hook projecting upwardly from the front portion of the platform as shown in FIGS. 1 through 4.

In an alternate embodiment of the present invention, the positioning means associated with the instrument 18 includes a recess in the forward upper surface of the platform 36 having a configuration substantially complementary to the actuating member 30. The instrument actuating member 30 is disposed at the proximal end of the instrument 18 and has downwardly-extending flanges 41 which are engageable with said recessed platform 36. In a preferred embodiment, the recessed platform is a rectilinear body having upper and lower sections 42 and 43 respectively which are separated by laterally inwardly projecting guide slots 44 extending at least a portion of the length of said platform 36.

Associated with the actuating member 30 in the alternate embodiment described above, in a means for reversibly engaging the proximal end 28 of the instrument. This allows the instrument to be manufactured of disposable material. Preferably, the proximal end of the instrument is equipped with a loop or the like which engages an upstanding retaining member 46 on the actuating member 30. A sleeve 47 is disposed at the proximal end of the instrument 18 in order that the instrument 18 fits snugly in the passageway 48.

Although the present invention has been described in detail with specific reference to its preferred embodiment, it will become obvious to one having ordinary skill in the art to make various modifications and changes thereof without departing from the spirit and scope of the invention.

I claim:

1. In a hand-held surgical device having an elongated housing defining a passageway between open-ended proximal and distal end portions; a suction connecting means disposed at said proximal end portion of the housing for applying suction to the passageway; a rectangular platform disposed at the proximal end portion of said housing and distal to the suction connecting means; said platform having a substantially flat upper surface, a bottom surface, side walls depending downwardly from said upper surface and extending to the bottom surface, and forward and rearward end walls depending downwardly from said top surface through which the passageway extends; and a suction adjusting means disposed in said platform, said adjusting means comprising an opening in the upper surface of said platform, and a second passageway extending from the opening in the surface of the platform to the passageway of the elongated housing, said opening communicating with the interior of the suction housing such that the reversible occlusion of said opening proportionately adjusts the magnitude of suction within the passageway of the housing; the improvement comprising a means for controlling the bi-directional movement of a surgical instrument longitudinally along the elongated housing, said controlling means comprising:

a recess in the forward upper surface of said platform adapted to receive a portion of the surgical instrument, said recess having an upper surface substantially parallel to the upper surface of the platform, a forward end adjacent the forward wall of the platform, and a downwardly depending rear wall extending from the upper surface of the platform to the upper surface of the recess; and a guide member disposed adjacent the forward end of the recess in the platform, said guide member having a passageway for allowing longitudinal movement of the surgical instrument therethrough, and a retaining means for preventing the outward deviation of said instrument from the platform.

2. The surgical device of claim 1 further comprising an elongated sheath disposed on the elongated housing, said sheath extending along a major portion of the distal end of the housing to the platform.

3. The surgical device of claim 1 wherein said housing is substantially cylindrical, and has an arcuate portion intermediate a straight distal end portion and the proximal end portion containing the platform.

4. The surgical device of claim 3 further comprising an elongated sheath disposed on the elongated housing, said sheath extending along a major portion of the distal end of the housing to the platform.

5. The surgical device of claim 4 wherein the guide member comprises a hook projecting upwardly from the forward end wall of said platform.

6. A hand-held surgical device having an elongated housing defining a passageway between open-ended proximal and distal end portions; a suction connecting means disposed at said proximal end portion of the housing for applying suction to the passageway; a rectangular platform disposed at the proximal end portion of said housing and distal to the suction connecting means; said platform having a substantially flat upper surface, a bottom surface, side walls depending downwardly from said upper surface and extending to the bottom surface, and forward and rearward end walls depending downwardly from said top surface through which the passageway extends; a suction adjusting means disposed in said platform, said adjusting means comprising an opening in the upper surface of said platform, and a second passageway extending from the opening in the surface of the platform to the passageway of the elongated housing, said opening communicating with the interior of the suction housing such that the reversible occlusion of said opening proportionately adjusts the magnitude of suction within the passageway of the housing; a surgical instrument having an elongated shaft having distal and proximal ends, a means disposed at the distal end of said shaft for performing surgical functions, and a means disposed at the proximal end of the shaft for actuating the movement of the instrument along the housing; and a means for controlling the bi-directional movement of the surgical instrument longitudinally along the elongated housing, said controling means comprising:

a recess in the forward upper surface of said platform receiving a portion of the surgical instrument, said recess having an upper surface substantially parallel to the upper surface of the platform a forward end adjacent the forward wall of the platform, and a downwardly depending rear wall extending from the upper surface of the platform to the upper surface of the recess; and a guide member disposed adjacent the forward end of the recess in the platform, said guide member having a passageway allowing longitudinal movement of the surgical instrument therethrough, and a retaining means for preventing the outward deviation of said instrument from the platform.

7. The surgical device of claim 6 further comprising an elongated sheath disposed on the elongated housing, said sheath extending along a major portion the distal end of the housing to the platform.

8. The surgical device of claim 7 wherein said housing is substantially cylindrical, and has an arcuate portion intermediate a straight distal end portion and the proximal end portion containing the platform.

9. The surgical device of claim 6 wherein the actuating means is rectangular and is substantially complementary to said recess; said actuating means having a substantially flat bottom surface slidably positioning the surgical instrument along said housing, and an upper surface having a plurality of detents therein.

10. The surgical device of claim 9 wherein said housing is substantially cylindrical, and has an arcuate portion intermediate a straight distal end portion and the proximal end portion containing the platform, said housing further comprising an elongated sheath disposed thereon, said sheath extending along a major portion of the distal end of the housing to the platform.

11. A surgical instrument for use in the hand-held surgical device of claim 1 wherein said instrument comprises:
an elongated shaft having distal and proximal ends;
a means disposed at the distal end of said shaft for performing surgical functions; and
a means disposed at the proximal end of the shaft for actuating the movement of the instrument along said housing; wherein the actuating means is rectangular and has a substantially flat bottom surface for slidably positioning the proximal end of said surgical instrument along the upper surface of said recess, an upper surface having a plurality of detents threin, and having overall dimensions substantially complimentary to said recess with the provision that the actuating means may move longitudinally between the downwardly depending rear wall and the guide member of said surgical device.

12. The surgical instrument of claim 11 wherein said surgical function means is a knife blade.

* * * * *